(12) United States Patent
Krause et al.

(10) Patent No.: US 7,935,512 B2
(45) Date of Patent: May 3, 2011

(54) COLICINOGENIC STRAIN OF E. COLI

(75) Inventors: Denis O. Krause, Winnipeg (CA); Martin Nyachoti, Winnipeg (CA)

(73) Assignee: The University of Manitoba, Winnipeg (CA)

( * ) Notice: Subject to any disclaimer, the term of this patent is extended or adjusted under 35 U.S.C. 154(b) by 189 days.

(21) Appl. No.: 12/298,921

(22) PCT Filed: May 1, 2007

(86) PCT No.: PCT/CA2007/000731
§ 371 (c)(1), (2), (4) Date: Apr. 3, 2009

(87) PCT Pub. No.: WO2007/124588
PCT Pub. Date: Nov. 8, 2007

(65) Prior Publication Data
US 2009/0324565 A1 Dec. 31, 2009

Related U.S. Application Data

(60) Provisional application No. 60/796,145, filed on May 1, 2006.

(51) Int. Cl.
*C12N 1/20* (2006.01)
*A01N 63/00* (2006.01)
*A23C 9/12* (2006.01)
*C12Q 1/02* (2006.01)

(52) U.S. Cl. .................. 435/252.33; 424/93.48; 426/61; 435/29

(58) Field of Classification Search ............. 435/252.33, 435/29; 426/2, 61
See application file for complete search history.

(56) References Cited

U.S. PATENT DOCUMENTS 5,965,128 A  10/1999  Doyle et al.

FOREIGN PATENT DOCUMENTS

WO  WO2005/074706  8/2005

OTHER PUBLICATIONS

Murinda, S.E. et al. Evaluation of colicins for inhibitory activity against diarrheagenic *Escherichi coli* strains, including serotype O157:H7. Appl Environ Microbiol, Sep. 1996, vol. 62, No. 9, pp. 3196-3202, ISSN:0099-2240.

Jin, L.Z. et al. A strain of *Enterococcus faecium* (18C23) inhibits adhesion of enterotoxigenic *Escherichia coli* k88 to porcine small intestine mucus. Appl Environ Microbiol, Oct. 2000, vol. 66, No. 10, pp. 4200-4204, ISSN:0099-2240.

Fairbrother, J. M. et al. *Escherichi coli* in postweaning diarrhea in pigs: an update on bacterial types, pathogenesis and prevention strategies. Anim Health Res Rev, Jun. 2005, vol. 6, No. 1, pp. 17-39, ISSN:1466-2523.

*Primary Examiner* — Delia M Ramirez
(74) *Attorney, Agent, or Firm* — Ade & Company Inc; Michael R. Williams

(57) ABSTRACT

Described herein is the isolation of colicin-producing strains of *E. coli* for use as probiotic treatments for the prevention of *E. coli* K88+ diarrhea. These strains of *E. coli*, designated as UM-17, and UM-19, express a filament and produce colicin but produce no compounds toxic to the host animal and as such inhibit the growth of *E. coli* K88+.

6 Claims, 1 Drawing Sheet

COLICINOGENIC STRAIN OF *E. COLI*

PRIOR APPLICATION INFORMATION

This application claims the benefit of U.S. Provisional Patent Application 60/796,145, filed May 1, 2006.

BACKGROUND OF THE INVENTION

Post-weaning diarrhea in weaned piglets is a significant production problem. Pigs that suffer from diarrhea typically have poor growth and/or become dehydrated, and in some instances will die. The problem is not so much an issue of mortality as it is one of lingering morbidity in the animal which means that it takes longer for the pig to be at the proper weight or condition to be shipped for slaughter, and hence is less profitable. One of the most frequent causes of this disease *Escherichia coli*. The most frequently occurring serotype is K88+ which attaches to the enterocyte via an F4-type fimbrea. Once attached it can made a variety of toxins which, when injected into the enterocyte, result in diarrhea.

SUMMARY OF THE INVENTION

According to a first aspect of the invention, there is provided an isolated colicin-producing *E. coli* strain selected from the group consisting of UM-17 and UM-19.

According to a second aspect of the invention, there is provided a probiotic for treatment of *E. coli* K88+-associated diarrhea comprising a colicin-producing *E. coli* strain selected from the group consisting of UM-17, UM-19 and combinations thereof.

According to a third aspect of the invention, there is provided a feed additive comprising a colicin-producing *E. coli* strain selected from the group consisting of UM-17, UM-19 and combinations thereof.

According to a fourth aspect of the invention, there is provided a method of treating *E. coli* K88+ diarrhea comprising administering an effective amount of a probiotic comprising a colicin-producing *E. coli* strain selected from the group consisting of UM-3, UM-17, UM-19 and combinations thereof.

DESCRIPTION OF THE PREFERRED EMBODIMENTS

Figure 1:
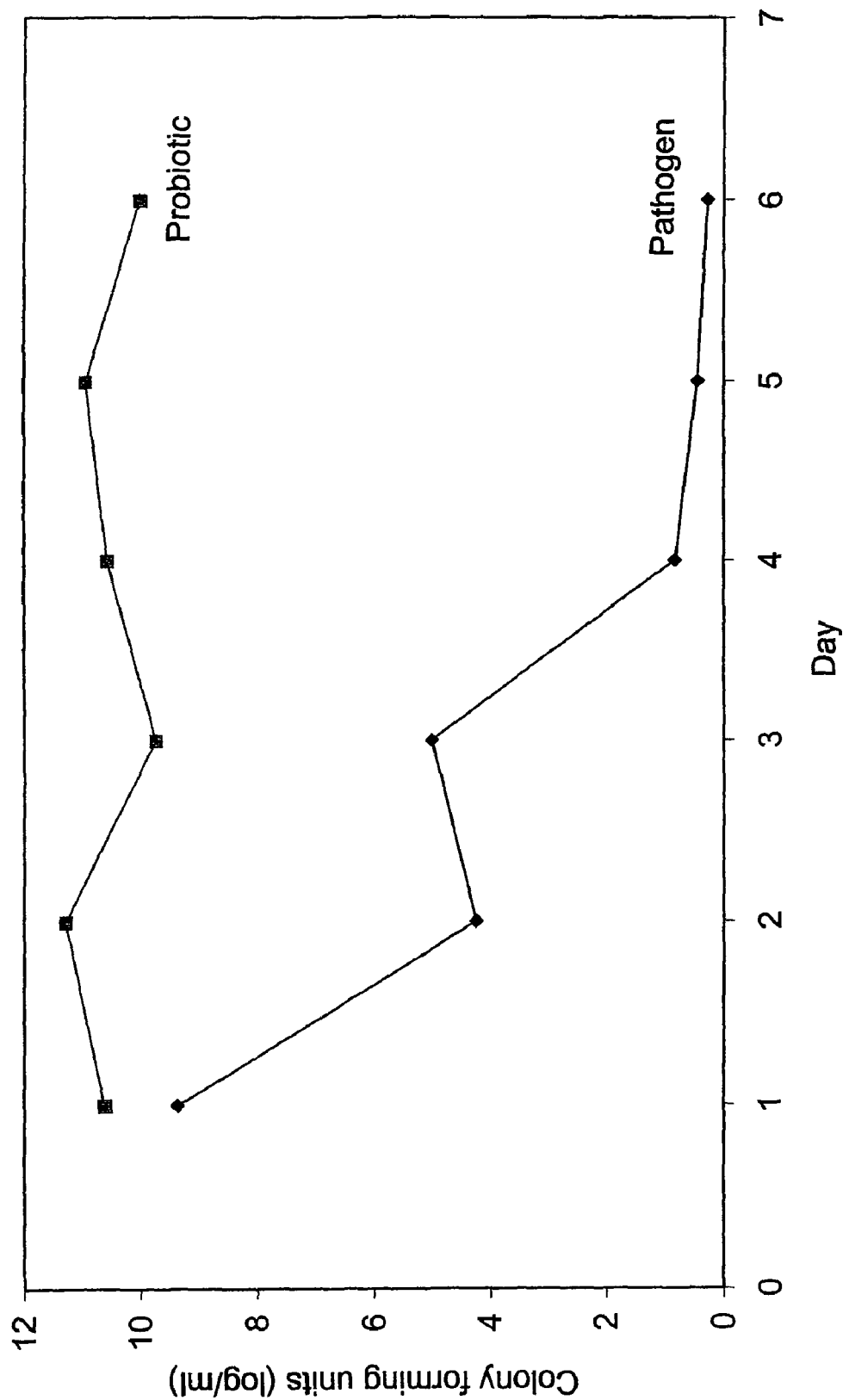
FIG. 1. Competition between the pathogen and probiotic. Bacteria were allowed to compete over a 24 h period, then 100 µl was transferred to a new chube. Over time, only the most competitive strain will survive.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is the isolation of colicin-producing strains of *E. coli* for use as probiotic treatments for the prevention of *E. coli* K88+ diarrhea. These strains of *E. coli*, designated as UM-17 and UM-19, express a filament and produce colicin but produce no compounds toxic to the host animal and as such inhibit the growth of *E. coli* K88+. It is of note that the above identified strains may be used alone or in combination and may also be combined with other treatments known in the art. It is noted that deposits of these strains were made on May 1, 2007 at the International Depositary Authority of Canada (National Microbiology Laboratory, Public Health Agency of Canada, 1015 Arlington Street, Winnipeg, Manitoba, Canada R3E 3R2) and they were assigned the following numbers: UM-17 IDAC 010507-01 and UM-19- IDAC 010507-02. The strains have been deposited under the Budapest Treaty and will be made available to the public under the conditions specified in 37 CFR 1.808.

According to one aspect of the invention, there is provided an isolated colicin-producing *E. coli* strain selected from the group consisting of UM-17 and UM-19. As will be appreciated by one of skill in the art, 'isolated' refers to the fact that the *E. coli* strains have been removed from their native environment, as discussed below. It is noted that these strains are also considered to be 'purified' or 'substantially purified' in that either all or substantially all of the bacteria are the same.

In other embodiments, the above-described strains are utilized in the manufacture of a probiotic for treatment of *E. coli* K88+-associated diarrhea. In these embodiments, the probiotic comprises an effective amount of at least one colicin-producing *E. coli* strain selected from the group consisting of UM-17, UM-19 and combinations thereof. As will be appreciated by one of skill in the art, 'an effective amount' is an amount that is sufficient to accomplish at least one of the following: inhibit *E. coli* K88+ growth, reduce *E. coli* K88+ growth rate within the animal, reduce severity of symptoms associated with *E. coli* K88+ infection, and the like.

In yet other embodiments, there is provided a method of treating *E. coli* K88+ diarrhea comprising administering to an animal in need of such treatment an effective amount of a probiotic comprising an effective amount of at least one colicin-producing *E. coli* strain selected from the group consisting of UM-17, UM-19 and combinations thereof.

The probiotic may be administered with the feed ration of the animal or may be combined with feed as well as other modes of administration of powders known in the art.

The colicinogenic strains identified are unique because they are also able to ferment amylase and/or inulin. These are both unusual phenotypes for *Escherichia coli* which means that it puts a downward pressure on *E. coli* growth. Our strains can ferment these sugars so that makes them more competitive in the gut. For example, the probiotic will work in pigs of between 14 and 56 days of age because the serotype K88 is only pathogenic in pigs of this age. Thus, in some embodiments of the invention, the probiotic as described above is administered in an effective amount to pigs between approximately 14 and 56 days old.

Fecal samples from pigs, hog lagoon manure, cattle and soil were plated out on *E. coli* selective chromogenic agar. After 18 h *E. coli* (purple colonies) and non-*E. coli* coliforms (blue, pink, and white colonies) were selected. *E. coli* (purple colonies) were picked from each positive tissue and subcultured in LB broth, and recultured on *E. coli*/coliform medium, and tested for reactivity to indole, methyl red, Vogues Proskauer, and citrate utilization. From this process 863 strains were positively identified as *E. coli*. To determine which of these strains were able to produce a colicin active against *E. coli* K88+, screening was done using a zone inhibition assay. In brief, the producer strain was grown in a single colony on LB agar for 24 h so that a colony of approximately 5 mm was visable on the agar. The indicator strain, K88+, was inoculated into soft LB agar (1%), mixed well, and then pored over the agar with the producer strain(s) on it. The plate was then allowed to incubate at 37° C. for 16 h. If a producer strain was positive, there was a clear zone around it indicating lack of growth. This procedure was carried out on all strains, and strains were ranked in descending order based on the size of the zone of inhibition. The top 80 strains were then screened for the presence of heat labile, heat stabile, and enterotoxin genes typically found in *E. coli* K88. Of these 80 strains 20 were selected for further investigation based on lack of toxins and inhibitory ability. These strains were screened with the API 50 system (bioMérieux) for the ability to ferment a range of 50 carbohydrates.

The probiotic can be administered as a freeze dried powder, prepared using means well-known in the art. In some embodiments, the powder may be coated, for example, alginate coated. In preferred embodiments, the probiotic powder is administered to animals in need of such treatment, for example, feed animals such as weaned pigs, at risk of or suspected of *E. coli* K88+ infection. It is of note that in these embodiments, the powder may be a food additive included in the feed ration of weaned pigs. This way the bacterium can be administered continuously, thus increasing its effect. Alternatively, in other embodiments, the bacterium could be administered as a stable paste, for example in a starch carrier, in high concentration, given on the day of weaning. Given that these strains have a carbohydrate selective pressure, the product may be most effective when fed with diets containing starch and/or inulin.

The invention will now be further described by way of example. However, the invention is not necessarily limited by the invention.

Example I

Animals, Housing, and Experimental Design

A total of 45 Cotswold piglets weaned at 17±1 d were obtained from the University of Manitoba's Glenlea swine research farm. The initial BW of the piglets was 4.82±0.6 kg. Five pigs were euthanized before the start of the experiment in order to generate the base line data for microbiology and other parameters. Forty piglets were divided into groups of two pigs per pen and were blocked on the basis of BW. Each pen had a plastic-covered expanded metal floor. In each block, three replicate pens were assigned to each dietary treatment in a completely randomized design. Pigs had unlimited access to feed and water throughout the 2 wk study. BW and feed disappearance were monitored daily and the results used to calculate ADG, ADFI, and G:F ratio. Room temperature was maintained at 29±1° C. throughout the study.

Experimental Diets

Each pen was assigned to one of the 4 wheat-soybean meal-based diets consisting of a control with an antibiotic (C) and three diets with no antibiotics but containing UM-17 and UM-19 as the probiotics (PRO), 14% potato starch (PS), or a combination of 14% potato starch and probiotics (PRO-PS). All experimental diets were formulated to meet NRC (1998) nutrient requirements for piglets weighing 7 to 12 kg (Table 1). Diets were mixed one week before the start of experiment.

Bacterial Culture, Oral Challenge and Health Status

Two strains (UM-17 and UM-19) having colicinogenic properties and a rapid growth on starch were selected. Results of in vitro competition assays revealed that UM-17 and UM-19 suppressed the *E. coli* K88 growth in the presence of starch. Fresh overnight probiotic cultures (50 ml of $9 \times 10^{10}$ cfu/ml per pen) were mixed with fresh feed each morning (Table 1).

Two *E. coli* K88+ strains (2-12 and I-36) were maintained aerobically in Luria Bertani (LB) broth at 39° C. An overnight culture was scaled up to 2 L by inoculating 5 ml of pre-culture. A sub-sample was taken and serially diluted (10-fold) and plated on LB agar to obtain colony forming units of the inoculant. On day 7 of the experiment (24 d old pigs), each pig received 6 ml ($2 \times 10^9$ cfu·mL$^{-1}$) of a bacterial suspension contained in a syringe attached to a polyethylene tube held in the back of the oral cavity. Severity of diarrhea was characterized by using the fecal consistency (FC) score method. Fecal consistency scoring (0, normal; 1, soft feces; 2, mild diarrhea; 3, severe diarrhea) was performed in a blinded fashion by two trained personnel with no prior knowledge of dietary treatment allocation. The presence of blood in feces was checked daily.

In Vitro Competition Assays

Isolates *E. coli* UM-17 and UM-19 were evaluated by in vitro competition assays with *E. coli* K88+ strain 2-12. UM-17 and UM-19 were made resistant to levofloxacin by repeated transfer in LB broth containing 1 µg·ml$^{-1}$ of levofloxacin. The MIC for levofloxacin was measured to be 0.05 µg·ml-1. *E. coli* 2-12 was not resistant to levofloxacin at 0.05 µg·ml$^{-1}$. Individual strains were maintained on minimal medium which contained (g·L$^{-1}$): glucose, 5; Na$_2$HPO$_4$, 6; KH$_2$PO$_4$, 3; NH$_4$Cl, 1; MgSO$_4$, 0.12; CaCl$_2$, 0.01. For competition assays strains were transferred at least three times on minimal medium with the growth substrate to be assayed. For example, for the competition assay with starch, the glucose in the minimal medium was substituted with starch. The *E. coli* 2-12 strain plus UM-17 or UM-19 was inoculated into medium to give a final cell concentration of approximately $10^6$ cfu·ml$^{-1}$ and incubated at 37° C. for 0, 12, 24, and 36 h. At the end of each incubation period, one ml of a well mixed culture was taken, serially diluted in triplicate in buffered peptone water, and plated onto LB-agar with or without 0.05 µg·ml$^{-1}$ levofloxacin at 37° C. for 16 h. All competition experiments were repeated on three separate occasions.

Blood Sampling and Blood Parameter Measurements

On day 0, five pigs were euthanized and blood was sampled via cardiac puncture using heparinized vacuum container tubes (Becton Dickinson, Rutherford, N.J., USA) to generate the base line data for blood parameters and packed cell volume (PCV). Blood collections from the forty experimental pigs was done three times; a day before inoculation, 24 h, and 48 h post inoculation, via jugular vein puncture using heparinized vacuum container tubes. The blood was processed by centrifugation at 2,000×g for 10 min at 4° C. to recover plasma. Plasma samples were stored at −70° C. until required for plasma urea nitrogen (PUN) determination using a Nova Stat profile M blood gas and electrolyte analyzer (Nova Biomedical Corporation, Waltham, Mass., USA). An additional blood sample was collected at the time of slaughter (day 14) via cardiac puncture and centrifuged at 3,000×g for 20 min at 5° C. to recover serum.

Chemical Analysis

Crude protein (CP) was analyzed using a Leco NS 2000 Nitrogen Analyzer (LECO Corporation, St. Joseph, Mich., USA). Gross energy (GE) was measured using a Parr adiabatic oxygen bomb calorimeter (Parr Instrument Co., Moline, Ill., USA).

While the preferred embodiments of the invention have been described above, it will be recognized and understood that various modifications may be made therein, and the appended claims are intended to cover all such modifications which may fall within the spirit and scope of the invention.

TABLE 1

Composition and nutrient analysis of experimental diets. (as-fed basis).

| | Diets[1] | | | |
|---|---|---|---|---|
| | C | Pro | 14% PS | Pro + 14% |
| Ingredients | | | | |
| Corn | 44.65 | 44.65 | 25.96 | 25.96 |
| Soybean meal | 32.8 | 32.8 | 39.0 | 39.0 |
| Whey powder | 12.0 | 12.0 | 12.0 | 12.0 |
| Limestone | 0.5 | 0.5 | 0.75 | 0.75 |
| Dical P | 0.75 | 0.76 | 1.0 | 1.0 |
| Vege. Oil | 5.0 | 5.0 | 5.0 | 5.0 |
| Lys-HCl | 0.19 | 0.19 | 0.19 | 0.19 |
| Fish meal | 3.0 | 3.0 | 1.0 | 1.0 |
| Vitamin Premix[2] | 0.5 | 0.5 | 0.5 | 0.5 |
| Mineral Premix[3] | 0.5 | 0.5 | 0.5 | 0.5 |
| L-Tryptophan | 0.1 | 0.1 | 0.1 | 0.1 |
| SP250[5] | 0.01 | — | — | — |
| Potato starch | — | — | 14.0 | 14.0 |
| Nutrient Analysis | | | | |
| CP | 21.37 | 21.96 | 21.09 | 21.95 |
| GE Kcal/Kg | 4336.17 | 4373.14 | 4165.69 | 4168.97 |

[1]Diets: C = control with antibiotics; Pro = control without antibiotics + probiotics; 14% = control without antibiotics + 14% potato starch; Pro + 14% = 14% + probiotics.
[2]Provided per kg of diet: 9,000 IU of vitamin A; 1,500 IU of vitamin D3; 18 mg of vitamin E; 1.5 mg of vitamin K; 250 mg of choline; 30 mg of niacin; 27.5 mg of calcium pantothenate; 9.4 mg of B2; 2 mg of B6; 25 μg of B12; 80 μg of biotin; 0.5 mg of folic acid.
[3]Provided per kg of diet: 18 mg copper, 110 mg zinc, 0.2 mg iodine, 110 mg iron, 50 mg manganese, and 0.3 mg selenium.
[4]Aureo sp250: Chlortetracycline, Penicillin (as penicillin G Procaine), Sulfamethazine (Alpharma Inc., Fort Lee, NJ, USA).

TABLE 2

Performance of early-weaned pigs fed different experimental diets.

| | Diets[1] | | | | | |
|---|---|---|---|---|---|---|
| Item | C | Pro | 14% PS | Pro + 14% | SEM[2] | P |
| Initial BW, kg | 4.62 | 4.70 | 4.84 | 4.90 | 0.24 | 0.8556 |
| Final BW, kg | 5.78 | 5.85 | 5.90 | 6.40 | 0.31 | 0.5030 |
| ADG, g/d | | | | | | |
| BI[3] | 86.25 | 94.50 | 54.97 | 122.50 | 23.13 | 0.2674 |
| AI[4] | 104.41 | 114.39 | 129.83 | 152.81 | 16.85 | 0.2368 |
| ADFI, g/d | | | | | | |
| BI | 351.23$^{ab}$ | 353.15$^{ab}$ | 281.85$^a$ | 413.70$^b$ | 42.39 | 0.2249 |
| AI | 451.68 | 436.80 | 455.44 | 512.48 | 37.49 | 0.5190 |

TABLE 2-continued

Performance of early-weaned pigs fed different experimental diets.

| | Diets[1] | | | | | |
|---|---|---|---|---|---|---|
| Item | C | Pro | 14% PS | Pro + 14% | SEM[2] | P |
| Gain:feed | | | | | | |
| BI | 0.22 | 0.23 | 0.20 | 0.29 | 0.04 | 0.4638 |
| AI | 0.24 | 0.26 | 0.28 | 0.30 | 0.03 | 0.5084 |

[1]Diets: as in table 1.
[2]pooled standard error of the means.
[3]BI = before inoculation.
[4]AI = after inoculation.
$^{ab}$Means within rows without common letters differ (P < 0.05).

TABLE 3

Effect of dietary treatments on fecal score data after inoculation with *E. coli* in early-weaned pigs.

| | Diets[1] | | | | | |
|---|---|---|---|---|---|---|
| Item | C | Pro | 14% PS | Pro + 14% | SEM[2] | P |
| Fecal Score[3] | | | | | | |
| 0 to 48 h | 0.45 | 0.50 | 0.86 | 0.81 | 0.22 | 0.4602 |
| 48 to 96 h | 0.99$^a$ | 1.23$^{ab}$ | 1.39$^b$ | 0.99$^a$ | 0.12 | 0.0835 |
| 0 to 96 h | 0.73$^a$ | 0.88$^{ab}$ | 1.15$^b$ | 0.90$^{ab}$ | 0.15 | 0.2784 |

[1]Diets: as in table 1.
[2]pooled standard error of the means.
[3]Fecal score: 0, normal; 1, soft feces; 2, mild diarrhea; 3, severe diarrhea
$^{ab}$Means within rows without common letters differ (P < 0.05).

The invention claimed is:

1. An isolated colicin-producing *E. coli* strain selected from the group consisting of UM-17 (IDAC 010507-01) and UM-19 (IDAC 010507-02).

2. A probiotic for treatment of *E. coli* K88+-associated diarrhea comprising a colicin-producing *E. coli* strain selected from the group consisting of UM-17 (IDAC 010507-01), UM-19 (IDAC 010507-02) and combinations thereof.

3. The probiotic according to claim 2 wherein the *E. coli* strain is in the form of a freeze-dried powder.

4. A feed additive comprising a colicin-producing *E. coli* strain selected from the group consisting of UM-17 (IDAC 010507-01), UM-19 (IDAC 010507-02) and combinations thereof.

5. The feed additive according to claim 4 wherein the *E. coli* strain is in the form of a freeze-dried powder.

6. A method of treating *E. coli* K88+ diarrhea comprising administering an effective amount of a probiotic comprising a colicin-producing *E. coli* strain selected from the group consisting of UM-17 (IDAC 010507-01), UM-19 (IDAC 010507-02) and combinations thereof.

* * * * *